US00PP28444P2

(12) United States Plant Patent
Kempler

(10) Patent No.: US PP28,444 P2
(45) Date of Patent: Sep. 26, 2017

(54) ***RUBUS* PLANT NAMED 'BC92915'**

(50) Latin Name: *Rubus idaeus*
Varietal Denomination: BC92915

(71) Applicant: Chaim Kempler, Richmond (CA)

(72) Inventor: Chaim Kempler, Richmond (CA)

(73) Assignee: HER MAJESTY THE QUEEN IN RIGHT OF CANADA AS REPRESENTED BY THE MINISTER OF AGRICULTURE AND AGRI-FOOD, Ottawa, Ontario (CA)

( * ) Notice: Subject to any disclaimer, the term of this patent is extended or adjusted under 35 U.S.C. 154(b) by 306 days.

(21) Appl. No.: 14/544,735

(22) Filed: Feb. 10, 2015

Related U.S. Application Data

(60) Provisional application No. 61/965,960, filed on Feb. 11, 2014.

(51) Int. Cl.
*A01H 5/08* (2006.01)

(52) U.S. Cl.
USPC ..... Plt./204

(58) Field of Classification Search
USPC ..... Plt./204
CPC ..... A01H 5/0887
See application file for complete search history.

(56) References Cited

PUBLICATIONS

GTITM UPOVROM Citation for 'BC92915' as per CA PBR 11-7404; Oct. 17, 2011; 1 page.*

* cited by examiner

*Primary Examiner* — Kent L Bell
(74) *Attorney, Agent, or Firm* — Penny J. Aguirre

(57) ABSTRACT

A new cultivar of *Rubus idaeus*, 'BC92915', that is characterized by its upright to semi-upright plant habit, its fruit that is large in size and conical to trapezoidal in shape, its fruit that matures early and machine harvests very well, and its resistance to aphids and root rot.

2 Drawing Sheets

Botanical classification: *Rubus idaeus.*
Cultivar designation: 'BC92915'.

BACKGROUND OF THE INVENTION

The present invention relates to a new and distinct cultivar of raspberry plant, botanically known as *Rubus idaeus* 'BC92915' and will be referred to hereinafter by its cultivar name, 'BC92915'.

The new cultivar was derived from a controlled breeding program by the Inventor at a nursery in Abbotsford, British Columbia, Canada. The overall purpose of the breeding program is to make selections of raspberry plants that are early season producers, commercially viable, and disease resistant. 'BC92915' arose from a cross made in 1992 between 'Malahat' (not patented) as the female parent and 'BC864115' (not patented) as the male parent. 'BC92915' was selected as a single unique plant in the summer of 1996 from amongst the seedling derived from the above cross.

Asexual propagation of the new cultivar was first accomplished under direction of the Inventor by root cuttings in Abbotsford, British Colombia in fall of 1996. Asexual propagation of the new cultivar by root cuttings and tissue culture has shown that the unique features are stable and reproduced true to type in successive generations.

SUMMARY OF THE INVENTION

The following traits have been repeatedly observed and represent the characteristics of the new cultivar. These attributes in combination distinguish 'BC92915' as a new and unique cultivar of *Rubus idaeus.*

1. 'BC92915' exhibits an upright to semi-upright plant habit.
2. 'BC92915' exhibits fruit that is large in size and conical to trapezoidal in shape.
3. 'BC92915' exhibits fruit that can be machine harvested very well.
4. 'BC92915' exhibits fruit that matures early.
5. 'BC92915' exhibits resistance to aphids and root rot.

The female parent of 'BC92915', 'Malahat', is similar to 'BC92915' in having fruit that is machine harvestable. The female parent of 'BC92915', 'Malahat', differs from 'BC92915' in being more susceptible to root rot, in having fruit that matures a few days earlier, and in having fruit that is smaller in size. The male parent of 'BC92915', 'BC864115', differs from 'BC92915' in having fruit that is more round in shape and in having fruit that matures later. 'BC92915' can be most closely compared to the *Rubus* cultivar 'Meeker' (not patented). 'Meeker' is similar to 'BC92915' in having fruit that is machine harvestable and in being resistant to root rot. 'Meeker' differs from 'BC92915' in having fruit that is smaller in size and that matures later.

BRIEF DESCRIPTION OF THE DRAWING

The accompanying colored photograph illustrates the overall appearance and distinct characteristics of the new *Rubus*, 'BC92915'. The photograph was taken of three year-old plants as grown outdoors in the ground in Abbotsford, British Colombia.

The photograph in

Figure 1:
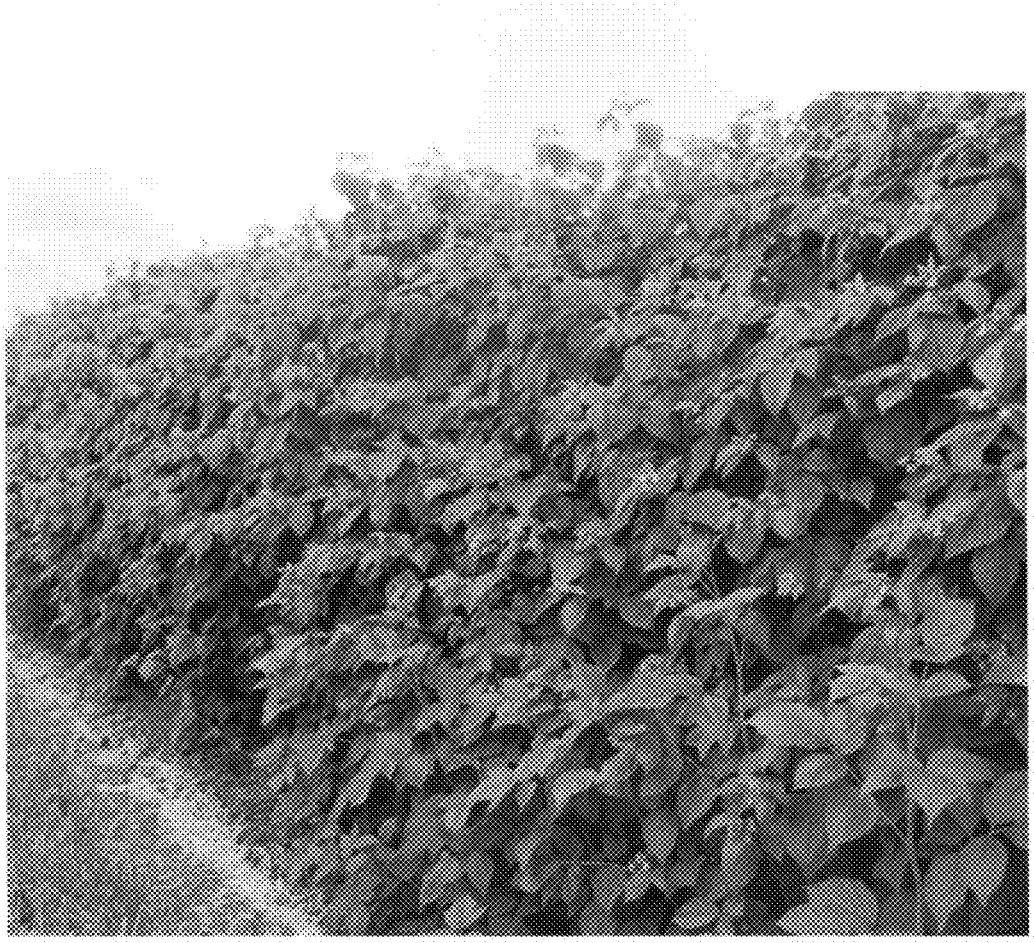
FIG. 1 provides a view of a row of plants of 'BC92915'.
Figure 2:
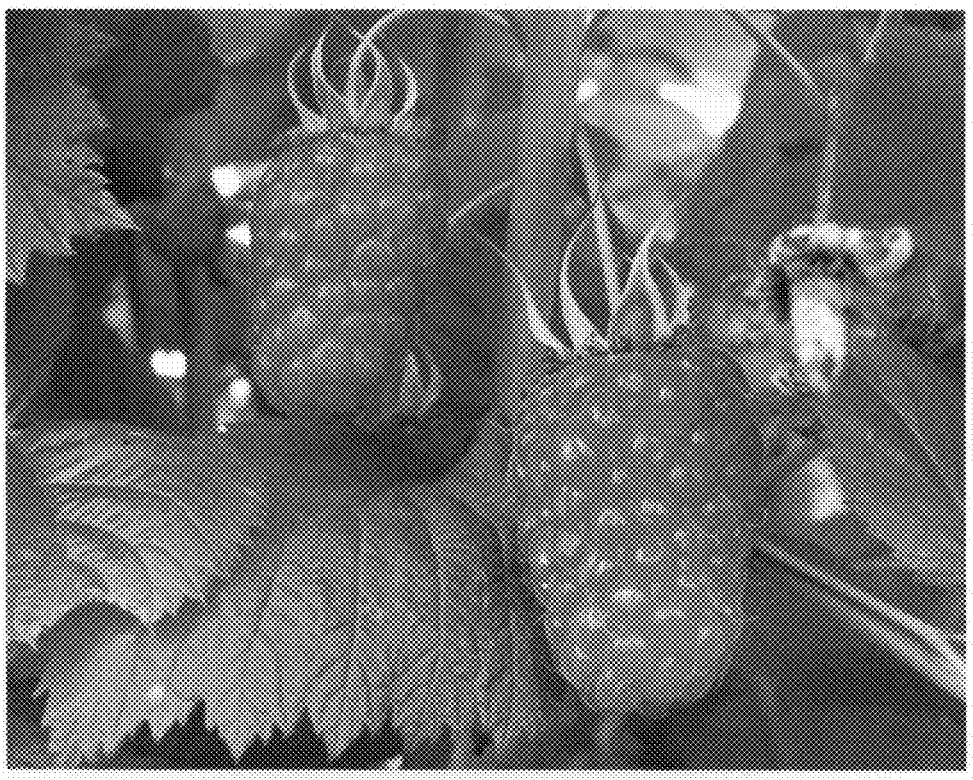
FIG. 2 provides a close-up view of the foliage of 'BC92915'.
Figure 3:
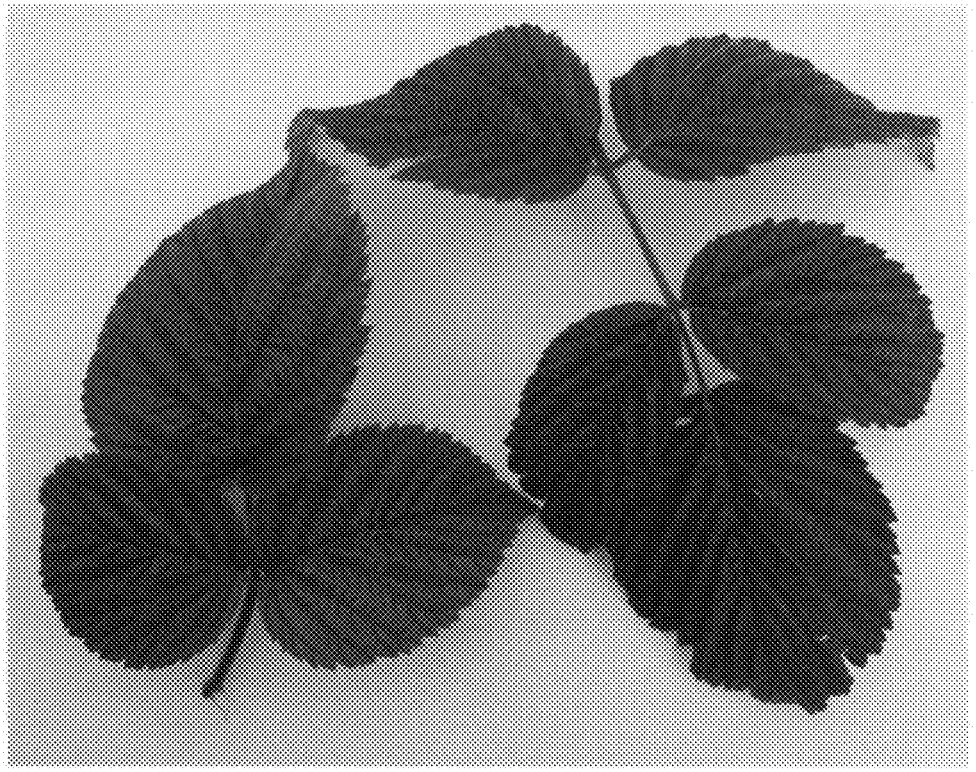
FIG. 3 provides a close-up view of the fruit of 'BC92915'.

The colors in the photographs are as close as possible with the photographic and printing technology utilized and the colors in the photograph may differ slightly from the color values cited in the detailed botanical description, which accurately describe the colors of the new *Rubus*.

DETAILED BOTANICAL DESCRIPTION OF THE PLANT

The following is a detailed description of three year-old plants of the new cultivar as grown outdoors in the ground in Abbotsford, British Colombia. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—Floricanes; Early to mid season; in Abbotsford, British Colombia, primocanes are non-blooming.

*Plant habit*.—Perennial, upright to semi-upright.

*Height and spread*.—Reaches an average of 2.6 m in height and 1.8 m in width.

*Hardiness*.—At least U.S.D.A. Zone 8b.

*Diseases and pests*.—Resistance to root rot (caused by *Phytophthora* sp.) and aphids (caused by *Amphorophora idaei*) has been observed.

*Root description*.—Fibrous and fine.

*Branching habit*.—Freely branching.

*Propagation*.—Tissue culture (preferred) or root cuttings.

*Growth rate*.—Moderate.

Stem description (floricanes: fruiting):

*Stem size*.—An average of 2.05 m in length and 7 mm in width with laterals an average of 65 cm in length and 5 cm in width.

*Stem color*.—145A.

*Stem surface*.—New and mature growth; glabrous with very sparse prickles colored the same as the stem position where they are located.

*Stipules*.—2 per petiole, very fine, an average of 5.6 mm in length, lanceolate in shape, 138B in color.

*Prickles*.—An average of <1 mm in length and 0.47 mm in width, average distance between prickles 26 mm.

Stem description (primocanes: non fruiting):

*Stem size*.—An average of 2.0 m in length and 7 mm in width, no laterals.

*Stem color*.—145B, fall color; 145B and suffused with 183A.

*Stem surface*.—New and mature growth; glabrous with waxy bloom with prickles on canes over 1 m in length.

*Stipules*.—Not observed.

*Prickles*.—1 to 2 mm in length and 0.5 mm in width, average distance between prickles 3 cm, slightly hooked and pointed downwards, 183A in color.

*Bud scales*.—187A in color.

Foliage description:

*Time of vegetative bud burst*.—Medium to early.

*Leaf shape*.—Ovate in overall form.

*Leaf division*.—3 or 5 leaflets.

*Leaf attachment*.—Petiolate.

*Leaf orientation*.—Outward to pendant.

*Leaf size*.—An average of 20.7 cm in length and 8.8 cm in width.

*Leaf quantity*.—An average of 3 per cane 5.2 cm in length.

*Internode length*.—An average of 3.7 cm.

*Leaflet shape*.—Ovate to oval.

*Leaflet base*.—Terminal leaflets; cuneate to cordate, lateral leaflets; oblique.

*Leaflet apex*.—Acute.

*Leaflet venation*.—Pinnate, color primarily matches leaf color.

*Leaflet margins*.—Doubly serrate.

*Leaflet arrangement*.—One terminal and 1 to 2 lateral pairs.

*Leaflet attachment*.—Sessile.

*Leaflet surface*.—Upper and lower surface slightly rugose.

*Leaflet color*.—Upper surface 135A, lower surface 191A.

*Leaflet size*.—Terminal; an average of 11.2 cm in length and 8.4 cm in width, lateral; an average of 9 cm in length and 5.2 cm in width.

*Leaflet substance*.—Thin.

*Petioles*.—Round in shape, an average of 5.1 cm in length and an average of 1 mm in width, sunny side 182A in color, shaded side 138D in color, all surfaces pubescent and sparsely covered with small prickles <1 mm in length and 138A in color.

*Rachis*.—An average of 9.4 cm in length and 0.08 mm in width, color; 145A, all surfaces pubescent and with 4.7 thorns per rachis.

Inflorescence description:

*Inflorescence*.—Raceme.

*Inflorescence size*.—An average of 23 cm in length (to base of inflorescence) and 2 cm in width.

*Lastingness of inflorescence*.—Average of 5 days.

*Rachis* (*peduncle*).—An average of 27.3 cm in length and 3.75 mm in width, surface moderately covered with prickles, 144C in color.

*Pedicels*.—An average of 2.2 cm in length and 2 mm in width, 144C in color. surface is sparsely covered with prickles.

*Flower buds*.—Triangular in shape with a wide flat bottom and apex narrowing to a point, 144A in color, an average of 1.1 cm in length and 8 mm in width.

*Flower type*.—Spreading calyx with a center of a ring of numerous upright stamens and with numerous pistils in the center, petals are quickly shed upon opening.

*Flower number*.—An average of 8 per raceme.

*Flower size*.—An average of 9 mm in depth and 2 cm in diameter.

*Bracts*.—An average of 3.2 cm in width, fused at base to edges of calyx, margins entire, color; 185D on upper and lower surface, upper and lower surface pubescent.

*Sepals*.—Five, an average of 1.1 cm in length and 4.6 mm in width, glabrous on upper and lower surfaces, thin, 185D in color on upper and lower surface, lanceolate in shape, entire margins, attenuate apex.

*Petals*.—Five, dropped just after flower opening, an average of 5 mm in length and 2.9 mm in width, ovate in shape, rounded apex, flat base, glabrous on upper and lower surfaces, thin, 155A in color.

*Receptacle*.—An average of 5.8 mm in diameter and 6.9 mm in depth.

*Androecium*.—An average of 80 stamens that form a concentric ring, inserted into calyx at base, an average of 5.2 mm in length, filaments are about 155A in color, anthers dorsifixed, pollen was not observed.

*Gynoecium*.—An average of 82 pistils, styles are an average of 4 mm in length, stigmas are very small and 145D in color, ovaries are attached to receptacle at base, ovate in shape, an average of 3.5 mm in length and diameter, with strongly pubescent surface with hairs.

Fruit description (berry):

*Fruit number*.—An average of 77 per fruiting branch.

*Fruit size*.—Aggregate an average of 1.9 cm in diameter and 2.7 cm in length.

*Fruit shape*.—Aggregate fruit is conical to trapezoidal.

*Fruit lateral attitude*.—Semi-erect.

*Fruit attachment*.—Moderate adherence.

*Druplets*.—An average of 96 per aggregate fruit, globose to rotund in shape, firm, an average of 3 mm in diameter and height, color when maturing; 148B, color when mature; 46A, surface is glossy, style and stigma; persistent at maturity, very fine.

*Persistence of sepals*.—Persistent.

*Receptacle*.—Round in shape (sits on calyx), stamens are inserted in the perimeter and ovaries are adhered in the center, an average of 8 mm in diameter and 2.5 cm in depth, 158B in color on upper and lower surface.

*Fruit maturity date*.—Mid summer.

*Seed*.—Oval in shape, 1 per druplet, 2 mm in length, 1 mm in width, 164B in color.

*Cropping frequency*.—Annually, produced on 1 year old wood.

*Fruit weight*.—Average of 4 g (ranges from 3 to 5).

*Fruit brix*.—13.

*Flavor*.—Sweet tart balance.

It is claimed:

1. A new and distinct cultivar of *Rubus* plant named 'BC92915' as herein illustrated and described.

* * * * *